US011103304B2

(12) United States Patent
Schultz

(10) Patent No.: US 11,103,304 B2
(45) Date of Patent: Aug. 31, 2021

(54) CATHETER WITH COMPOSITE INSERT SUPPORT MEMBER

(71) Applicant: BIOSENSE WEBSTER (ISRAEL) LTD., Yokneam (IL)

(72) Inventor: Jeffrey William Schultz, Chino, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 672 days.

(21) Appl. No.: 15/622,018

(22) Filed: Jun. 13, 2017

(65) Prior Publication Data

US 2018/0353238 A1    Dec. 13, 2018

(51) Int. Cl.
*A61B 90/00* (2016.01)
*A61B 18/00* (2006.01)
*A61B 18/14* (2006.01)

(52) U.S. Cl.
CPC ............... *A61B 18/1492* (2013.01); *A61B 2018/00029* (2013.01); *A61B 2018/00357* (2013.01);
(Continued)

(58) Field of Classification Search
CPC .............. A61B 18/1492; A61B 18/14; A61B 2018/00029; A61B 2018/00351;
(Continued)

(56) References Cited

U.S. PATENT DOCUMENTS 7,377,906 B2    5/2008  Selkee
8,357,152 B2    1/2013  Govari et al.
(Continued)

FOREIGN PATENT DOCUMENTS

EP    2 862 534 A1    4/2015
EP    3 023 070 A1    5/2016

OTHER PUBLICATIONS

Extended European Search Report issued in corresponding EP Application No. 18177189.0, dated Nov. 30, 2018, 8 pages.
(Continued)

*Primary Examiner* — Linda C Dvorak
*Assistant Examiner* — Nicholas S Borsch
(74) *Attorney, Agent, or Firm* — Lewis Roca Rothgerber Christie LLP

(57) ABSTRACT

An irrigated electrophysiology catheter has a tip electrode having a shell, and a support member configured to plug the shell and support one or more tip components and/or facilitate their functions. Advantageously, the support member has an electrically-conductive interface portion and an insert-molded portion, wherein the interface portion, typically constructed of a precious metal alloy, is structurally minimized, yet still configured for electrical connection with the shell and the lead wire, so as to reduce the amount and hence the cost of its manufacture, whereas the insert-molded portion is constructed of a significantly less-costly material and is readily configured with micro-complex 3-D geometry adapted to support tip structure and functions including irrigation, force sensing and temperature sensing, as a further cost savings in the manufacturing of the tip electrode by reducing materials, labor and time.

11 Claims, 10 Drawing Sheets

(52) U.S. Cl.
CPC ............ *A61B 2018/00577* (2013.01); *A61B 2018/00815* (2013.01); *A61B 2018/00821* (2013.01); *A61B 2018/00839* (2013.01); *A61B 2090/065* (2016.02); *A61B 2218/002* (2013.01)

(58) Field of Classification Search
CPC ........... A61B 2018/00357; A61B 2018/00577; A61B 2018/00815; A61B 2018/00821; A61B 2018/00791; A61B 2018/00839; A61B 5/042; A61B 5/6852; A61B 2090/065; A61B 2218/002; A61B 2018/1405; A61B 2018/00773
See application file for complete search history.

(56) References Cited

U.S. PATENT DOCUMENTS

| | | | |
|---|---|---|---|
| 8,792,962 | B2 | 7/2014 | Esguerra et al. |
| 2008/0255540 | A1 | 10/2008 | Selkee |
| 2010/0063441 | A1* | 3/2010 | Grunewald ............ A61B 5/042 604/95.04 |
| 2010/0168827 | A1 | 7/2010 | Schultz |
| 2011/0130648 | A1 | 6/2011 | Beeckler et al. |
| 2011/0270244 | A1 | 11/2011 | Clark |
| 2014/0187893 | A1* | 7/2014 | Clark ..................... A61B 5/042 600/373 |
| 2016/0143690 | A1* | 5/2016 | Schultz .............. A61B 18/1492 606/41 |
| 2020/0038100 | A1* | 2/2020 | Hillukka ............ A61B 18/1492 |

OTHER PUBLICATIONS

EP Office action issued in corresponding EP Application No. 18177189.0, dated Apr. 30, 2019, 6 pages.

Cater, B., "Insert Molding vs Traditional Injection Molding" Manufacturing Tomorrow, dated Apr. 11, 2017, 5 pages XP055582562; url:https://www.manufacturingtomorrow.com/article/2017/04/insert-molding-vs-traditional-injection-molding/9443 [retrieved on Mar. 31, 2021].

* cited by examiner

CATHETER WITH COMPOSITE INSERT SUPPORT MEMBER

FIELD OF INVENTION

The present invention relates to electrophysiologic (EP) catheters, in particular, EP catheters for ablating cardiac tissue.

BACKGROUND

Electrode catheters have been in common use in medical practice for many years. Diagnosis and treatment of cardiac arrythmias by means of electrode catheters include mapping the electrical properties of heart tissue and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall.

In a two-step procedure—mapping followed by ablation—electrical activity at locations within the heart is typically sensed and measured by advancing a catheter containing one or more electrical sensors (or electrodes) into the heart, and acquiring data at a multiplicity of locations. These data are then utilized to select the tissue target areas at which ablation is to be performed.

In use, the electrode catheter is inserted into a major vein or artery, e.g., the femoral artery, and then guided into the chamber of the heart which is of concern. A reference electrode is provided, generally taped to the patient's skin or provided on the ablation catheter or another catheter. Radio frequency (RF) current is applied to the ablation electrode of the catheter, and flows through the surrounding media, i.e., blood and tissue, toward the reference electrode. The distribution of current depends on the amount of electrode surface in contact with the tissue, as compared to blood which has a higher conductivity than the tissue.

The distal tip electrode of conventional irrigated catheters employs a two-part configuration, with a thin dome electrode shell having an opening and an interior cavity, and an insert support member that sits in and plugs the opening sealing the interior cavity. The shell, which may be formed by any suitable method, including, for example, stamping, deep drawing or conventional machining, and the insert support member are both constructed of electrically-conductive material, including palladium/platinum alloy or similar precious metal alloy so that electrical connection supplying electrical energy to the insert support member is conducted to the shell during ablation procedures. The insert support member thus serves to provide a physical connection to the shell allowing laser welding or other suitable permanent connection between the shell and the insert support member and providing an electrical connection to the shell. With conventional catheters enabled with multiple functions, including, irrigation, position sensing, temperature sensing and RF ablation, the insert support member incorporates a complex geometry in order to accommodate a multitude of components in a very compact region.

Not only does the use of precious metal alloys increase the cost of the insert support member, but intricate, micromachining to produce the complex geometry can increase the cost of manufacture significantly. Accordingly, there is a desire for an insert support member which can be formed from a less-costly material and by a less-costly method, while meeting the requirements of complex geometry, electrical conductivity and permanent connection. There is a desire for the insert support member to have a structure and configuration better suited for low cost, high volume manufacturing and further, for integration of components such as a temperature sensor and reduction of additional components such as polyimide insulation spacers and tubes.

SUMMARY OF THE INVENTION

An irrigated electrophysiology catheter has a tip electrode having a shell, and a support member configured to plug the shell and support one or more tip components and/or facilitate their functions. Advantageously, the support member has an electrically-conductive interface portion and an insert-molded portion, wherein the interface portion, typically constructed of a precious metal alloy, is structurally minimized, yet still configured for electrical connection with the shell and the lead wire, so as to reduce the amount and hence the cost of its manufacture, whereas the insert-molded portion is constructed of a significantly less-costly material and is readily configured with micro-complex 3-D geometry adapted to support tip structure and functions including irrigation, force sensing and temperature sensing, as a further cost savings in the manufacturing of the tip electrode by reducing materials, labor and time.

In some embodiments of the present invention, an electrophysiology catheter has an elongated catheter body, a lead wire, and a tip electrode. Configured for irrigation, the tip electrode and has a shell and a support member. The shell has a proximal opening and an interior cavity. The support member advantageously has an electrically-conductive interface portion, such as a precious metal alloy, and an insert-molded portion of a plastic material, the interface portion being in electrical connection with the shell and the lead wire, and the interface portion having a peripheral portion engaged with the shell at the proximal opening.

In some detailed embodiments, the insert-molded portion includes a distal portion in the interior cavity of the shell.

In some detailed embodiments, the insert-molded portion includes a proximal portion proximal of the peripheral portion of the interface portion.

In some detailed embodiments, the insert-molded portion has a fluid passage.

In some detailed embodiments, the insert-molded member has a fluid aperture.

In some detailed embodiments, the insert-molded portion has a longitudinal passage configured to receive a tensile component.

In some detailed embodiments, the insert-molded portion has a proximal extension having an outer surface with an outer surface of the interface portion.

In some detailed embodiments, the insert-molded portion has a circumferential indentation configured to receive a ring electrode, including, for example, an insert-molded ring electrode.

In some detailed embodiments, the insert-molded portion has an annular flange configured to receive a portion of a component, including, for example, a force sensor.

In some detailed embodiments, the insert-molded portion has a notch configured to allow passage of the lead wire connected to the ring electrode.

In some detailed embodiments, the insert-molded portion has a recess configured to receive a component, including, for example, a thermistor.

In some embodiments of the present invention, a method of manufacturing an electrophysiology catheter with a tip electrode, comprising (a) providing a shell, the shell having an interior cavity, (b) providing a support member with an interface portion of one material, including a precious metal alloy, and an insert-molded support member of another material, including plastic, including (i) configuring a thin sheet to form the interface portion, and (ii) insert molding the interface portion with the insert-molded portion, wherein the interface portion is configured to engage with the shell with a distal portion of the insert-molded portion positioned in the interior cavity.

In some detailed embodiments, the configuring a thin sheet to form the interface portion includes providing the interface portion with an electrical connection member.

In some detailed embodiments, the insert molding the interface portion includes exposing a portion of the electrical connection member for connection to a lead wire.

In some detailed embodiments, the electrical connection member projects from an opening formed in the interface portion and extends proximally through the opening.

In some detailed embodiments, the configuring a thin sheet to form the interface portion includes forming the interface portion with an opening through which the insert-molded portion extends.

In some detailed embodiments, the configuring a thin sheet to form the interface portion includes forming an interlock projection configured to be surrounded by the insert-molded portion.

In some detailed embodiments, the configuring a thin sheet to form the interface portion includes forming a peripheral portion configured for an interference fit with a proximal rim of the shell.

In some detailed embodiments, the peripheral portion has a step having a distal portion to engage with the proximal shell.

In some detailed embodiments, the method further comprises insert molding a ring electrode onto the insert-molded portion.

In some detailed embodiments, the method further comprises insert molding a connector sleeve onto the insert-molded portion.

In some embodiments, a method of manufacturing an electrophysiology catheter with a tip electrode, comprises (a) providing a shell, the shell having an interior cavity, (b) providing a support member with an interface portion of a metal alloy and an insert-molded portion of a plastic material, including: (i) configuring a thin sheet of the metal alloy to form the interface portion, and (ii) insert molding the interface portion with the plastic material to form the insert-molded portion, wherein the interface portion is configured to engage with the shell with a distal portion of the insert-molded portion positioned in the interior cavity of the shell, and (c) mounting the shell onto the support member, wherein the interface portion is engaged with the shell and a distal peripheral portion of the interface portion has an interference fit with a proximal opening of the shell.

In some detailed embodiments, wherein the insert molding the interface portion with the plastic material to form the insert-molded portion includes forming a circumferential indentation on an outer surface on the insert-molded portion, and the method further comprises insert molding a ring electrode in the circumferential indentation.

In some detailed embodiments, wherein the insert molding the interface portion with the plastic material to form the insert-molded portion includes forming a recess, and the method further comprises insert molding a thermistor in the recess.

In some detailed embodiments, wherein the insert molding the interface portion with the plastic material to form the insert-molded portion includes forming a fluid passage.

In some detailed embodiments, wherein the insert molding the interface portion with the plastic material to form the insert-molded portion includes forming a fluid aperture.

In some detailed embodiments, wherein the insert molding the interface portion with the plastic material to form the insert-molded portion includes forming an annular flange configured to receive a distal end of a force sensor.

In some detailed embodiments, the mounting the shell onto the support member includes forming a laser welding bond between the shell and the interface portion.

In some detailed embodiments, the configuring a thin sheet of the metal alloy to form the interface portion includes forming an electrical connection member, and the insert molding the interface portion with the plastic material to form the insert-molded portion includes exposing at least a portion of the electrical connection member configured for connection to an electrical energy conduit.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
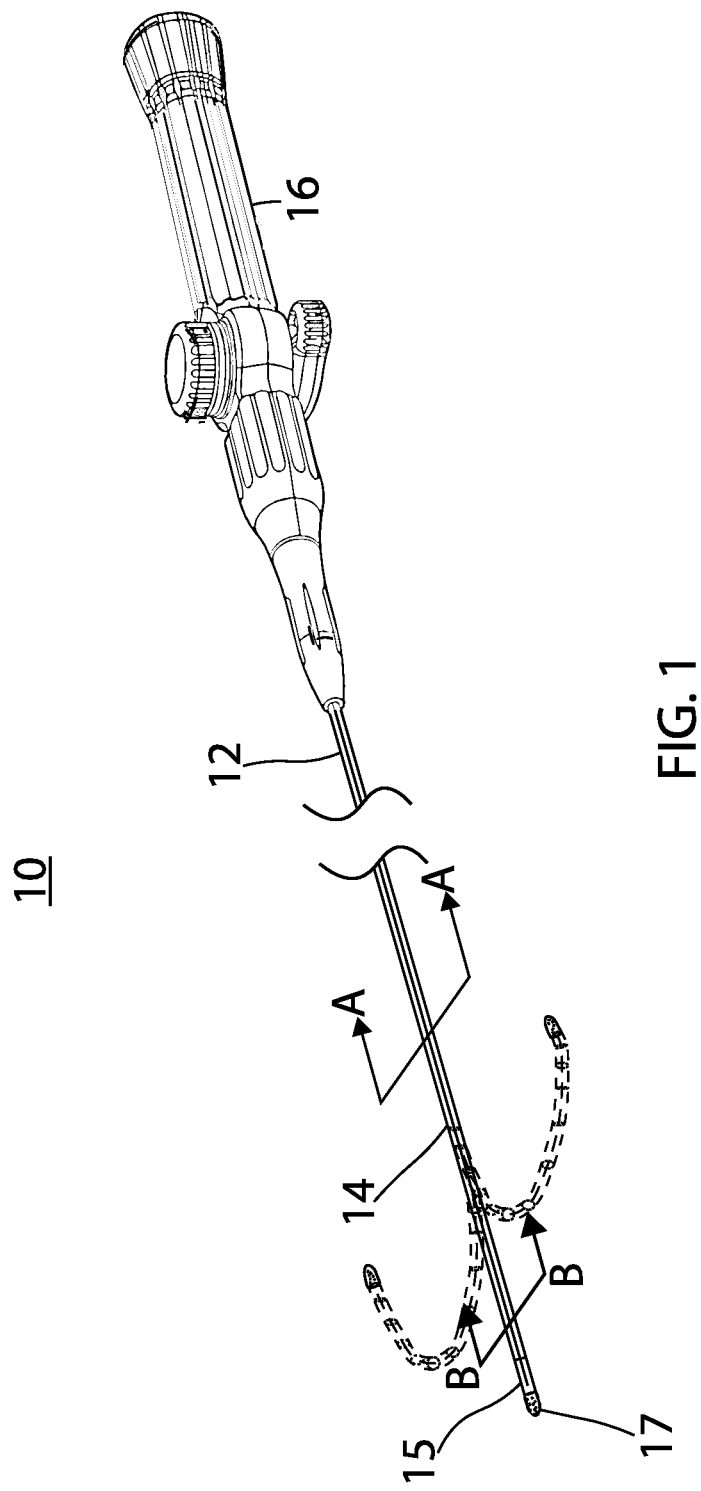
FIG. 1 is a perspective view of a catheter of the present invention, in accordance with an embodiment.

FIG. 1 illustrates an embodiment of a catheter 10 with an improved irrigation-cooled ablation tip electrode. The catheter has an elongated catheter body 12 with proximal and distal ends, an intermediate deflectable section 14 at the distal end of the catheter body 12, and a distal section 15 with a tip electrode 17. The catheter also includes a control handle 16 at the proximal end of the catheter body 12 for controlling deflection (single or bi-directional) of the intermediate section 14 relative to the catheter body 12.

Figure 2:
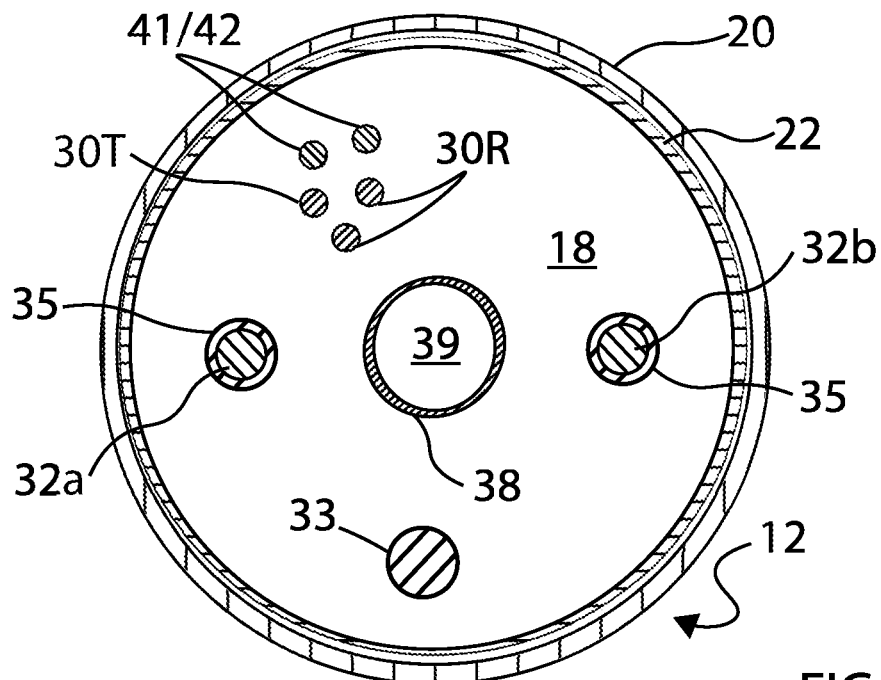
FIG. 2 is an end cross-sectional view of a catheter body of the catheter of FIG. 1, taken along line A-A.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller members (e.g., puller wires), lead wires, and any other desired wires, cables or tubings. If desired, the inner surface of the outer wall 20 is lined with a stiffening tube 22 to provide improved torsional stability. A disclosed embodiment, the catheter has an outer wall 20 with an outer diameter of from about 0.090 inch to about 0.94 inch and an inner diameter of from about 0.061 inch to about 0.065 inch.

Components that extend between the control handle 16 and the deflectable section 14 pass through the central lumen 18 of the catheter body 12. These components may include lead wires 30T and 30R (for the tip electrode 17 and one or more ring electrodes 21 proximal of the tip electrode), an irrigation tubing 38 with lumen 39 for delivering fluid to the tip electrode, a cable 33 for a position sensor 34 carried in or near the distal section 15, puller wires 32a, 32b for deflecting the intermediate section 14, and a pair of thermocouple wires 41, 42 to sense temperature at the distal section 15.

Figure 3:
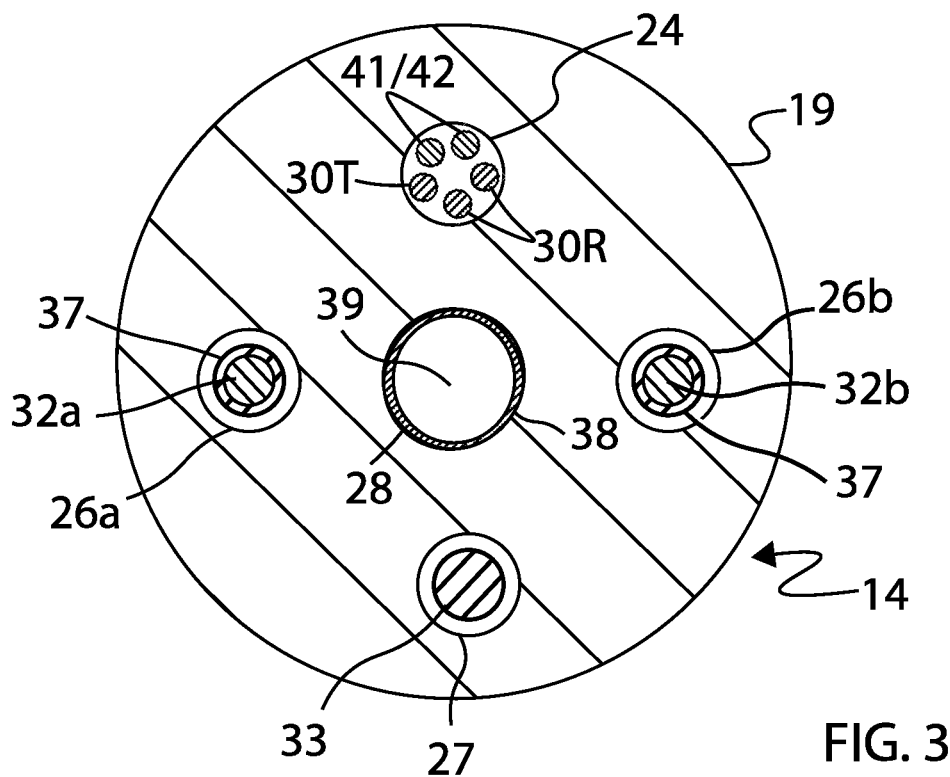
FIG. 3 is an end cross-sectional view of an intermediate deflection section of the catheter of FIG. 1, taken along line B-B.

Illustrated in FIG. 3 is an embodiment of the intermediate section 14 which comprises a short section of tubing 19. The tubing has multiple lumens, for example off-axis lumens 24, 26a, 26b, 27 and on-axis lumen 28. The lumen 24 carries the lead wires 30T and 30R, and the thermocouple wires 41 and 42. The lumen 27 carries the position sensor cable 33. The lumen 28 carries the irrigation tubing 38. The lumen 26a carries a puller wire 32a for deflection of the intermediate section. For bi-directional deflection, the diametrically-opposing lumen 26b carries a second puller wire 32b. It is understood that the plurality and arrangement of the lumens of the tubing 19 may vary as needed or appropriate. For example, in other embodiments, the tubing 19 may have two opposing lumens for puller wires, with two more lumens about 90 degrees therefrom, for routing all other components.

The tubing 19 of the intermediate section 14 is made of a suitable non-toxic material that is more flexible than the catheter body 12. A suitable material for the tubing 19 is braided polyurethane, i.e., polyurethane with an embedded mesh of braided stainless steel or the like. The size of each lumen is not critical, but is sufficient to house the respective components extending therethrough.

Each puller wire 32a and 32b has a lubricious coating, e.g. of Teflon®. The puller wires can be made of any suitable metal, such as stainless steel or Nitinol and the Teflon coating imparts lubricity to the puller wire. The puller wire preferably has a diameter ranging from about 0.006 to about 0.010 inch.

As shown in FIG. 3, the portion of each puller wire in the catheter body 12 passes through a compression coil 35 in surrounding relation to its puller wire. Each compression coil 35 extends from the proximal end of the catheter body 12 to at or near the proximal end of the intermediate section 14. The compression coils are made of any suitable metal, preferably stainless steel, and are tightly wound on themselves to provide flexibility, i.e., bending, but to resist compression. The inner diameter of the compression coil is preferably slightly larger than the diameter of the puller wire. Each portion of the puller wires distal of the compression coil 35 may extend through a respective protective sheath 37 to prevent the puller wire from cutting into the tubing 19 of the intermediate section 14 during deflection.

Figure 4:
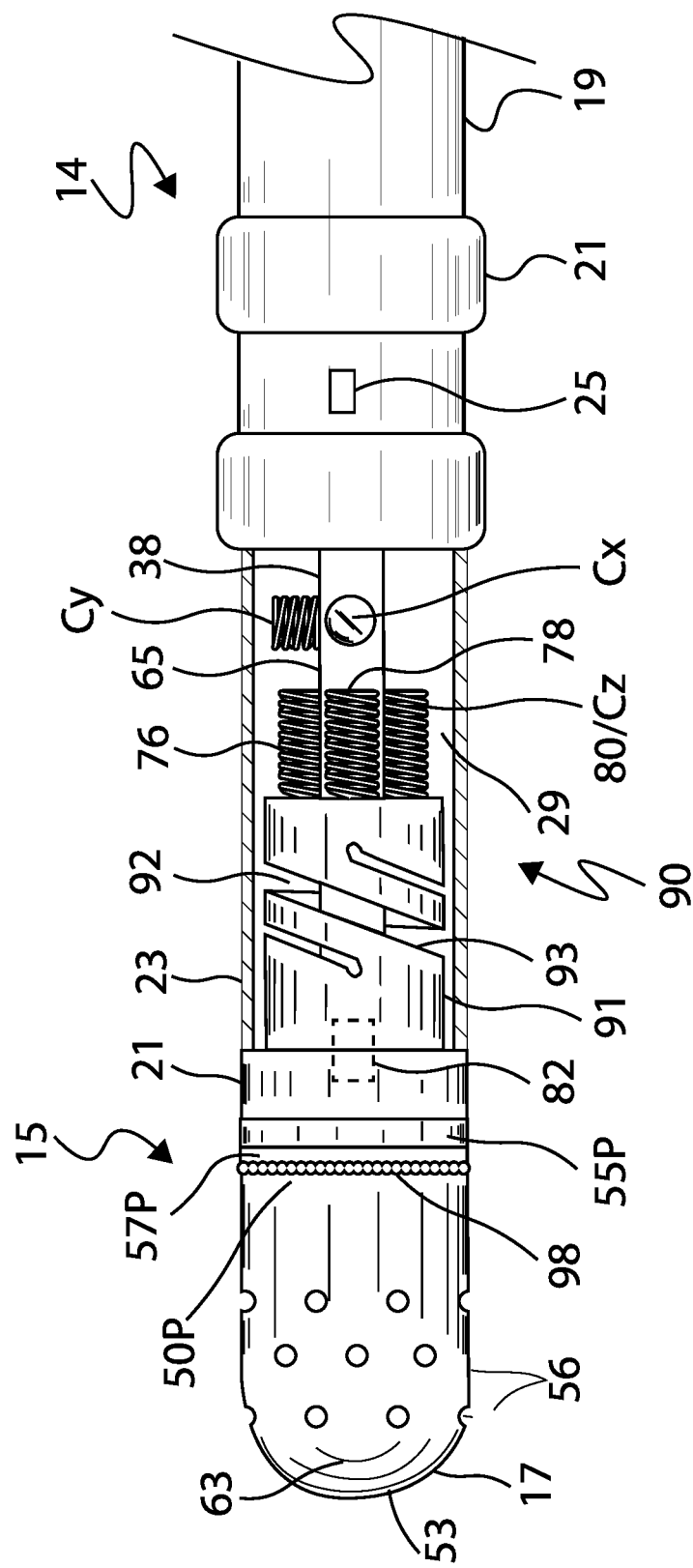
FIG. 4 is a side view of a distal section of the catheter of FIG. 1, with part(s) broken away.

Proximal ends of the puller wires 32a and 32b are anchored in the control handle 16. Distal ends of the puller wires 32a and 32b are anchored at or near the distal end of the tubing 19 of the intermediate section 14, as understood by one of ordinary skill in the art. In some embodiments, T-bars 25 may be used to anchor the distal ends of the puller wires near the distal end of the tubing 19, as shown in FIG. 4). In other embodiments, one or more components or features may be molded in the tip electrode 17 for looping or otherwise anchoring the puller wires, as described further below. Separate and independent longitudinal movements of the puller wires relative to the catheter body 12, which results in, respectively, deflection of the intermediate section 14 along a plane, are accomplished by suitable manipulation of a deflection member of the control handle 16. Suitable deflection members and/or deflection assemblies are described in co-pending U.S. Publication No. US2010/0168827 A1, published Jul. 1, 2010, entitled DEFLECTABLE SHEATH INTRODUCER, and U.S. Publication No. US2008/0255540 A1, published Oct. 16, 2008, entitled STEERING MECHANISM FOR BI-DIRECTIONAL CATHETER, the entire disclosures of both of which are hereby incorporated by reference.

Figure 6A:
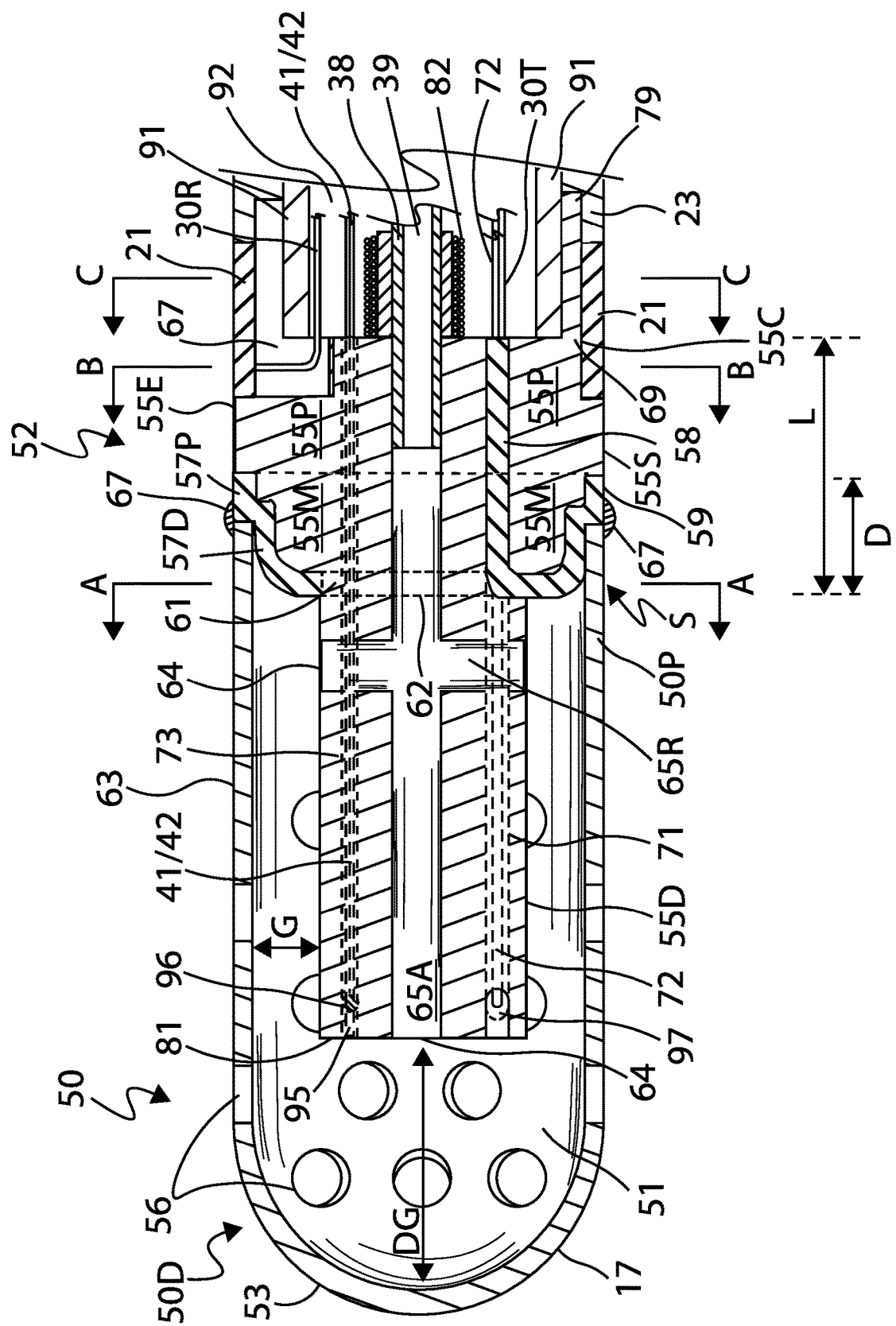
FIG. 6A is a side cross-sectional view of a shell and an insert member, in accordance with an embodiment of the present invention.

With reference to FIG. 4 and FIG. 6A, at the distal end of the intermediate section 14 is the distal tip section 15 that includes the tip electrode 17 and a relatively short piece of non-conductive connector tubing or sleeve 23 between the tip electrode 17 and the intermediate section 14. In the illustrated embodiment, the connector tubing 23 has a single lumen 29 which receives a distal end of the position sensor cable 33 and allows passage of components including electrode lead wires 30T and 30R, thermocouple wires 41 and 42, and the irrigation tubing 38 into the distal section 15 and tip electrode 17. The single lumen 29 of the connector tubing 23 allows these components to reorient themselves as needed from their respective lumens in the intermediate section 14 toward their location within the distal section 15 and tip electrode 17. In the disclosed embodiment, the tubing 23 is a protective tubing, having a length ranging between 6 mm and 12 mm.

The connector tubing 23 also houses a force sensor 90. Aspects of a force sensor similar to force sensor are described in U.S. Pat. No. 8,357,152, issued on Jan. 22, 2013 to Govari et al., entitled CATHETER WITH PRESSURE SENSING, and in U.S. Patent Publication No. 2011/0130648, to Beeckler et al., filed Nov. 30, 2009, entitled CATHETER WITH PRESSURE MEASURING TIP, both of whose disclosures are incorporated herein by reference.

The force sensor 90 includes a resilient coupling member 91, which forms a spring joint. In some embodiments, the coupling member 91 has hollow cylindrical form with a central lumen 92 therethrough. Coupling member 91 typically has one or more helices 93 cut or otherwise formed in the member, so that the member behaves as a spring. In some embodiments, the coupling member 91 is formed of a superelastic alloy, such as nickel titanium (Nitinol), within force sensor 90.

Figure 5:
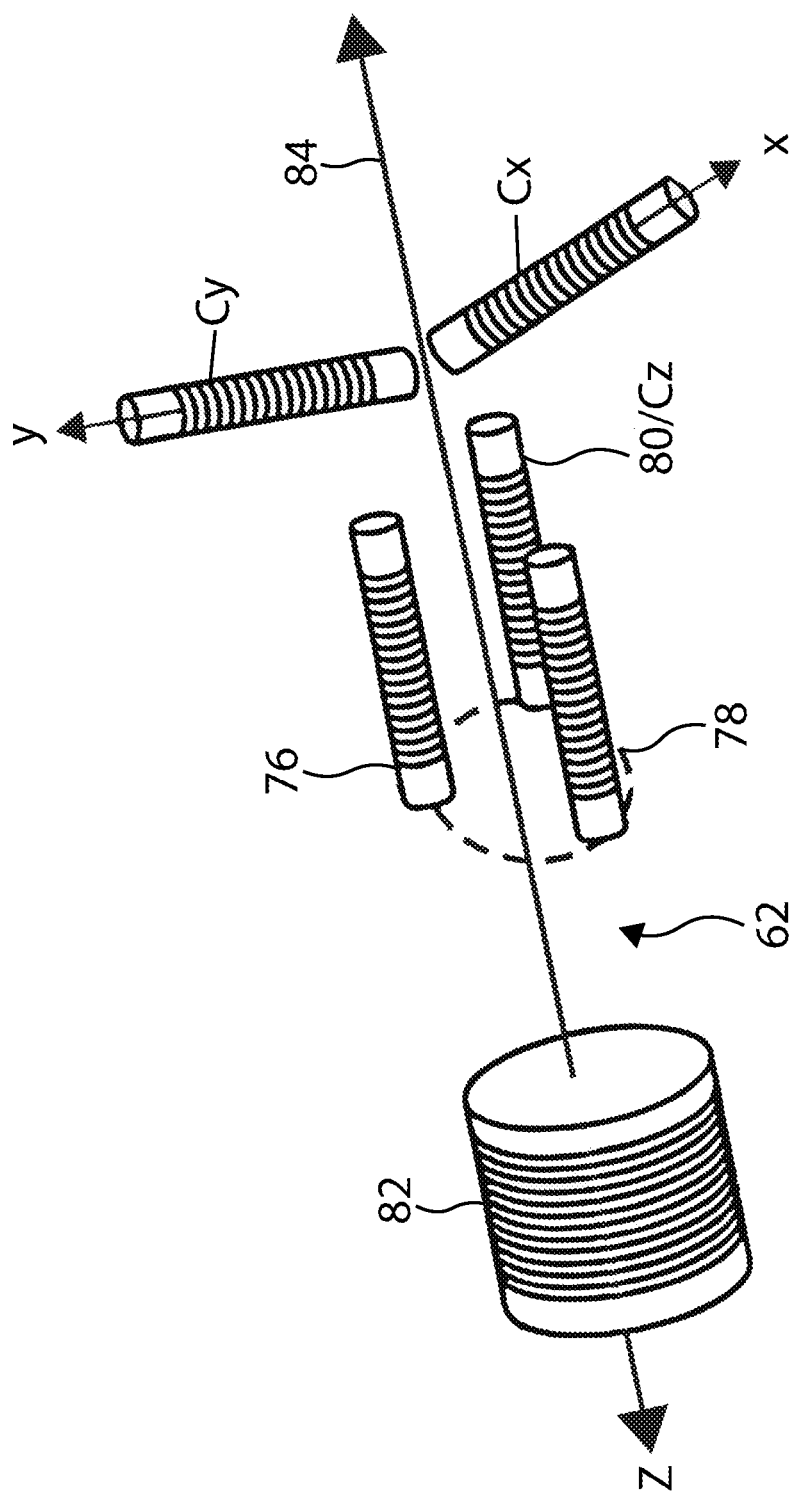
FIG. 5 is a schematic representation of magnetic coil components housed, in the distal section, in accordance with one embodiment.

With reference to FIG. 5, the force sensor 90 includes a joint sensing assembly comprising coils 76, 78, 80 and 82 that provides accurate reading of any dimensional change in axial displacement and angular deflection in the spring joint, including when the tip electrode 17 is angularly displaced from a longitudinal axis 84 of the catheter, such as then the tip electrode comes into contact with tissue. These coils are one type of magnetic transducer that may be used with the catheter. A "magnetic transducer," in the context of the present patent application and in the claims, means a device that generates a magnetic field in response to an applied electrical current and/or outputs an electrical signal in response to an applied magnetic field. Although the embodiments described herein use coils as magnetic transducers, other types of magnetic transducers may be used in alternative embodiments, as will be apparent to those skilled in the art.

The coils in the sensing assembly are divided between two subassemblies on opposite sides of the spring joint. One subassembly comprises coil 82 distal of the spring joint, which is driven by a current, via a wire (included in the cable 33), to generate a magnetic field. This field is received by a second subassembly, comprising coils 76, 78 and 80, which are located proximal of the spring joint, in a section of the connector tubing 23 that is spaced axially apart from and proximal of the coil 82. The term "axial," as used in the context of the present patent application and in the claims, refers to a direction along or parallel to the longitudinal axis 84 of the catheter. The coil 82 typically lies on-axis with the longitudinal axis 84.

The coils 76, 78 and 80 are fixed in connector tubing 23 at the same proximal distance from the coil 82 but at different radial locations. (The term "radial" refers to coordinates about the longitudinal axis 84.) Specifically, in the illustrated embodiment, the coils 76, 78 and 80 are all located in the same plane perpendicular to the longitudinal axis 84 but at different equi-azimuthal angles about the longitudinal axis 84, that is, the three coils are spaced azimuthally 120 degrees apart at the same axial distance from the coil 82 along the longitudinal axis 84.

The coils 76, 78 and 80 generate electrical signals in response to the magnetic field transmitted by coil 82. These signals are conveyed by wires (part of the cable 33) extending proximally from the distal section 15, through the lumen 24 of the intermediate section 14, through the lumen 18 of the catheter body 12 and into the control handle 16. The signals are processed by a remote processor in order, for example, to measure the axial displacement of spring joint along the longitudinal axis 84, as well as to measure the angular deflection of the joint from the longitudinal axis 84.

From the measured displacement and deflection, the processor is able to evaluate, typically using a previously determined calibration table, a magnitude and a direction of the force on the spring joint.

The same processor (or another processor) detects and measures the location and orientation of distal section 15. The method of measurement may be by any convenient process known in the art. In one embodiment, magnetic fields generated external to a patient create electric signals in elements in the distal section 15, and the processor uses the electric signal levels to determine the distal section location and orientation. Alternatively, the magnetic fields may be generated in the distal section 15, and the electrical signals created by the fields may be measured external to patient. As also shown in FIG. 5, the elements in distal section 12 that are used to position and locate the distal section) 12 include orthogonal coil $C_x$ aligned with the X axis, orthogonal coil $C_y$ aligned with the Y axis, and one of the coil 76, 78 and 80 (in addition to their use as elements of force sensor), for example, the coil 80 aligned with the Z axis as orthogonal coil $C_z$. The coils $C_x$, $C_y$, $C_z$/80 are housed in the connector tubing 23, within the lumen 68 of the coupling member 60. These coils are the sensing components of the electromagnetic position sensor 34 to which the cable 33 is connected. In some embodiments, the catheter includes a single axial sensor (SAS) cable assembly in lieu of the cable 33 and the electromagnetic position sensor 34 for position and location sensing. A SAS cable assembly suitable for use is described in U.S. Pat. No. 8,792,962, titled CATHETER WITH SINGLE AXIAL SENSORS, the entire disclosure of which is incorporated herein by reference.

Figure 7A:
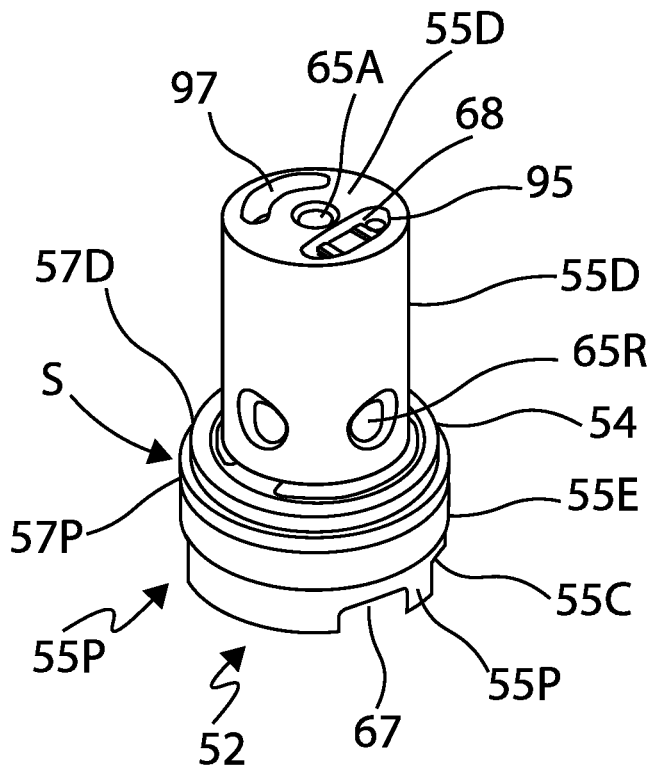
FIG. 7A is a perspective view of an insert member, in accordance with an embodiment of the present invention.

With reference to FIG. 4, FIG. 6A and FIG. 7A, the irrigated tip electrode 17 has a two-piece construction that includes an electrically-conductive dome shell 50 and a support member 52. The shell 50 has a hollow cylindrical body 50B with an open proximal portion (or rim) 50P in communication with an interior cavity 51 defined by a closed distal portion 50D with a dome atraumatic distal end 53. Formed in wall 63 of the shell 50 are a plurality of fluid exit ports 56 that allow fluid communication between the interior cavity and outside the shell 50. The support member 52 advantageously has a configuration including an electrically-conductive interface portion 54 and an insert-molded portion 55 which functions as a unitary body.

Figure 8:
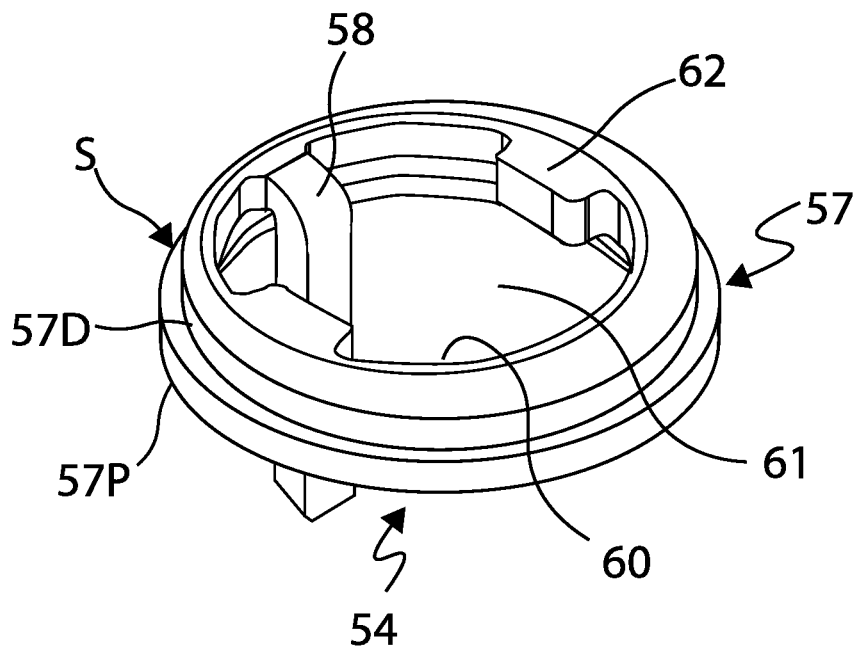
FIG. 8 is a perspective view of an interface portion of the insert member, in accordance with an embodiment of the present invention.
Figure 9A:
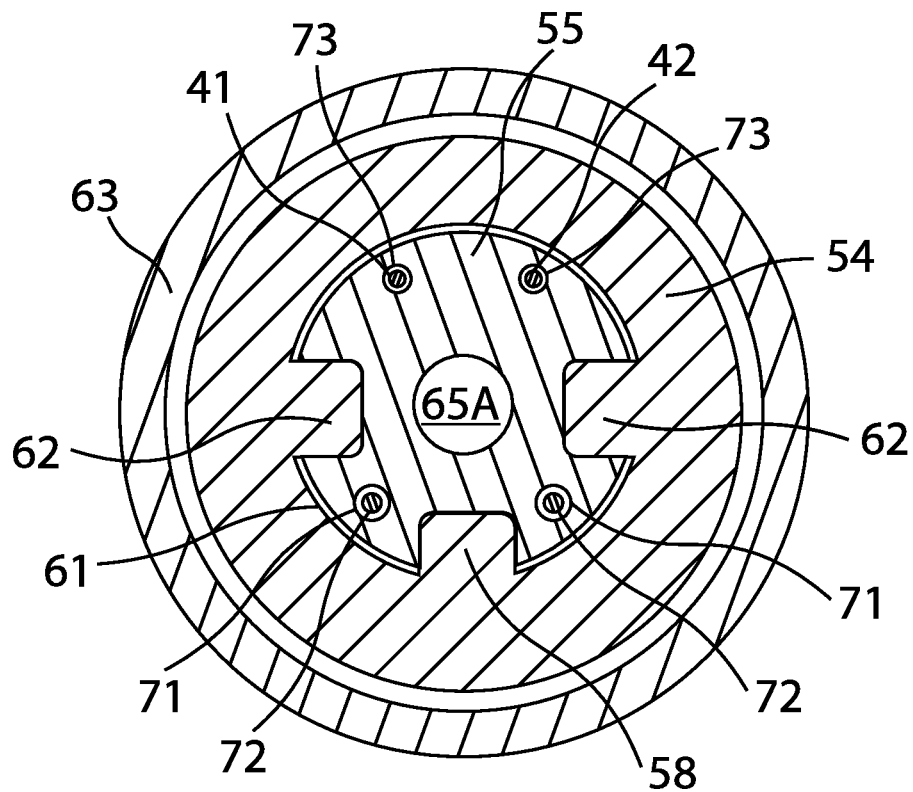
FIG. 9A is an end cross-sectional view of the tip electrode of FIG. 6A, taken along line A-A.
Figure 9B:
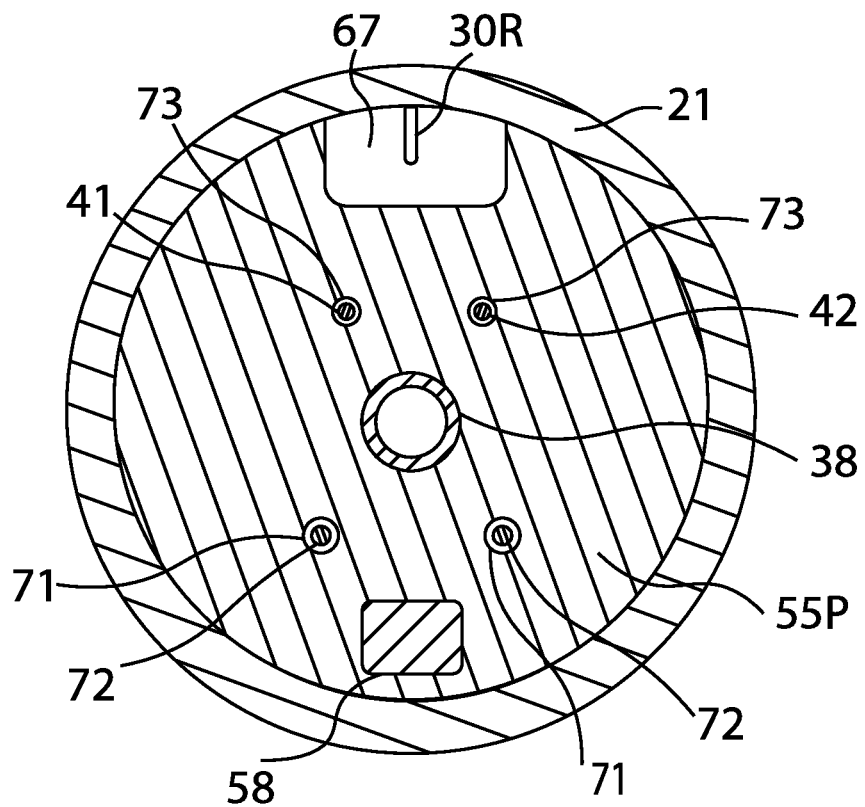
FIG. 9B is an end cross-sectional view of the tip electrode of FIG. 6A, taken along line B-B.
Figure 9C:
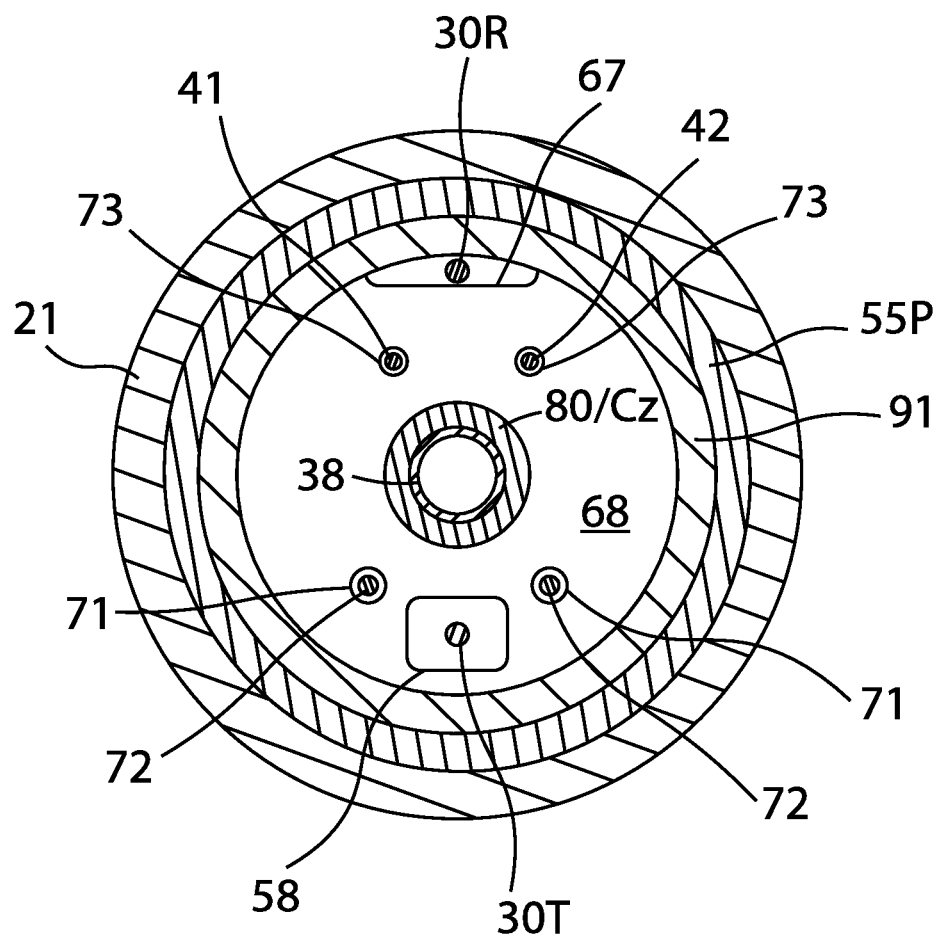
FIG. 9C is an end cross-sectional view of the tip electrode of FIG. 6A, taken along line C-C.

The interface portion 54 (perhaps best seen in FIG. 8) mates or engages with the shell 50 for electrical conduction. In some embodiments, as illustrated in FIG. 6A, the interface portion 54 has an annular configuration (e.g., a ring) such that a peripheral portion 57 provides an interference fit with the proximal opening portion or rim 50P of the shell 50, sealing the rim 50P so that the interior cavity 51 provides an internal plenum chamber within the shell 50. In some embodiments, a cross-section of the peripheral portion 57 includes a step S defining a relatively narrower (distal) annular portion 57D that is immediately distal of the rim 50P of the shell, and a relatively wider (proximal) annular portion 57P inside of the rim 50P of the shell. The step S provides a circumferential surface to which the proximal rim 50P of shell 50 is attached, e.g., via a laser weld 98, in its circumferential entirety to provide a durable attachment of the shell to the interface portion 54 and thus to the catheter 10.

The interface portion 54 includes an electrical connection member or tab 58 to which lead wire 30T is connected for energizing the interface portion 54 and thus also the shell 50 in engagement with the interface portion 54. A distal inner edge 60 (see FIG. 8) of the peripheral portion 57 surrounds an opening 61 through which the insert-molded portion 55 extends. To interlock the interface portion 54 with the insert-molded portion 55, the inner edge 60 is formed with one or more projections 62 surrounded by the insert-molded portion 55 and around which the insert-molded portion 55 is formed, as explained below in further detail.

In some embodiments, the interface portion 54 is formed from a thin sheet of an electrically-conductive, biocompatible material, such as a metal alloy or precious metal alloy. The shell 50 is also constructed of the same or similar electrically-conductive biocompatible material. A suitable biocompatible metal alloy includes an alloy selected from stainless steel alloys, noble metal alloys and/or combinations thereof. In one embodiment, the alloy comprises about 80% palladium and about 20% platinum by weight. In an alternate embodiment, the alloy comprises about 90% platinum and about 10% iridium by weight. In some embodiments, the shell 50 is formed by deep-drawing manufacturing process which produces a sufficiently thin but sturdy shell wall that is suitable for handling, transport through the patient's body, and tissue contact.

Figure 6B:
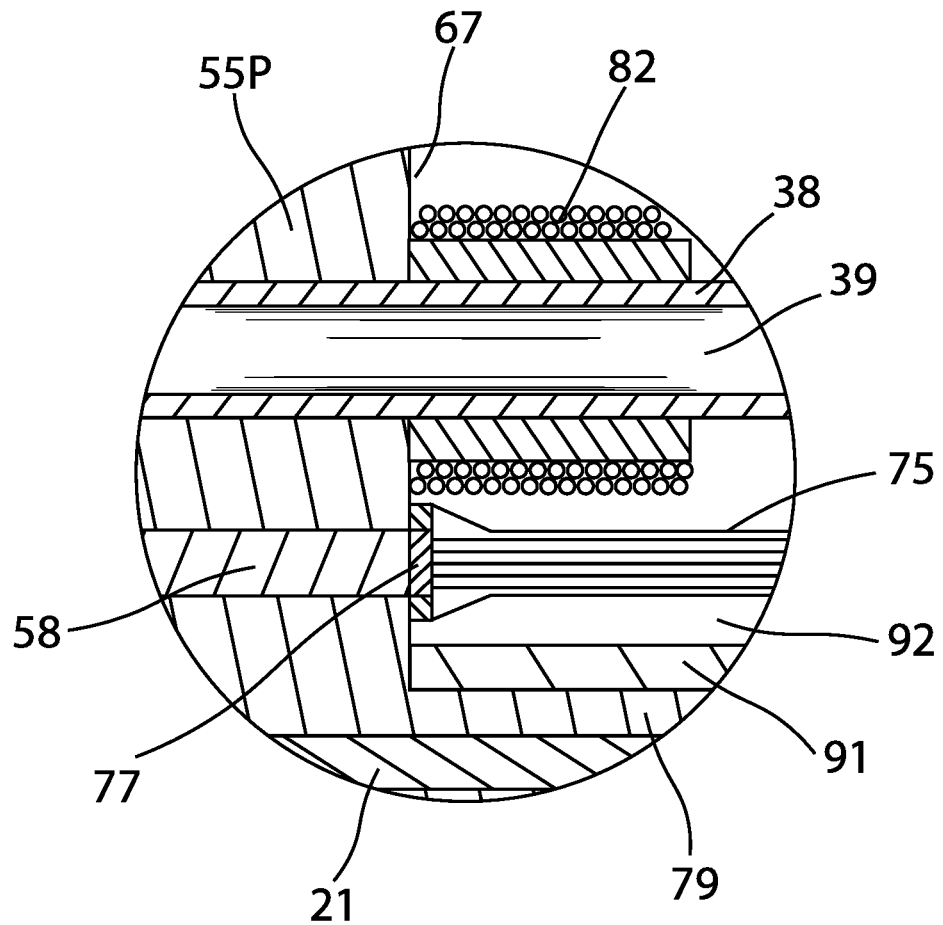
FIG. 6B is a detailed side cross-sectional view of a proximal portion of an insert member and a flex circuit, in accordance with another embodiment of the present invention.

Suitable methods for manufacturing the interface portion 54 from the thin sheet include, for example, stamping, deep drawing and other conventional methods, to provide the interface portion with its inner and outer edges and 3-D configuration. In particular, the manufacturing method provides portions of the thin sheet within the region of the opening 61 to form the tab 58 and the interlock projections 62. In the illustrated embodiment, the portion forming the tab 58 is subsequently bent or otherwise shaped with a U-bend to extend proximally through the opening 61 at an angle generally perpendicular to a plane defined by the opening 61. In some embodiments, that the interface portion 54 is configured and sized such the length L of the tab 58 exceeds the depth D of the interface portion 54 (see FIG. 6A) to provide easier access when the lead wire 30T is attached to the tab 58, with the recognition that an extension portion can be added to the tab 58 where there is a need or desire for the length L to be greater than the diameter of the opening 61. It is further understood that the tab 58 may be configured in a variety of shapes and sizes so long as the lead wire 30T can be connected to it, for example, by soldering a wire bond or any other conventional methods. Electrical energy or signals may be transmitted to or from the interface portion 54 by any suitable conduit, including a flex circuit 75, as shown in the embodiment of FIG. 6B, where a portion of the flex circuit 75 is placed on the proximal face 79 with the remainder portion extending, for example, proximally in the lumen 92 of the coupling member 91, and the flex circuit 75 has one or more thru-vias 79 for receiving and soldering to the tab 58 and/or the thermocouple wires 41 and 42.

The insert-molded portion 55 has a distal portion 55D that is distal of the interface portion 54, a main portion 55M that is within the interface portion 54, and a proximal portion 55P that is proximal of the interface portion 54. In some embodiments, the distal portion 55 is configured generally as a solid cylinder that extends into the shell 50, occupying space within the interior cavity 51 defined by the surrounding shell 50. The distal portion 55D has a predetermined diameter or girth and a length that leave a circumferential gap G and a distal gap DG between the distal portion 55D and the shell 50. In some embodiments, the main portion 55M extends between the opening 61 and a proximal end of the peripheral portion 57 of the interface portion 54, and is in conformity with the inner surface of the interface portion 54, e.g., via injection-molding. The main portion 55M is configured to block the opening 61. Notably, the main portion 55M may be formed around the tab 58 without interfering with the conductive connection of the tab 58 and the lead wire 30T. That is, the insert molding of the interface portion 54 with a plastic material, to form the insert-molded portion 55 leaves a portion of the tab 58 exposed and accessible for connection of a suitable electrical conduit.

Having an injected-molded body, the insert-molded portion 55 is integrated with the interface portion 54 and thus the members 54 and 55 function and perform as a single, unitary body and component. In comparison to prior support members constructed entirely of a metal alloy, the support member 52 with the members 54 and 55 herein provides similar effective functions, including plugging the shell, enabling a durable and conductive shell attachment, and providing desirable and/or necessary complex 3-D geometry in accommodating other functions and/or component layouts in the tip electrode, but at a significantly lesser cost due to savings in supply and manufacturing costs. Supply costs are reduced with lesser use of precious metal alloy in the support member, and manufacturing costs are reduced by replacing micro-drilling with insert molding, including micro-insert molding, the latter of which can produce more intricate and detailed 3-D geometry.

In some embodiments, the 3-D geometry includes one or more fluid apertures 64 and one or more interconnected fluid passages 65 extending through the length of the insert-molded portion 55. In the illustrated embodiment, the insert-molded portion 55 includes a longitudinal, on-axis fluid passage 65 having a proximal opening at the proximal face 79 that receives a distal end of the irrigation tubing 38. The fluid passage 65 passes through the opening 61 of the interface portion 54 and branches into axial passage 65A and radial passages 65R which are in communication with the fluid apertures 64, so that fluid passing from the irrigation tubing 38 can exit the fluid apertures 64 and enter the plenum chamber in the interior cavity 51 of the shell 50, and exit the shell 50 via exit ports 56 to outside of the tip electrode 17. The shell 50 and the plug 52 facilitate the provision of a plenum condition within the interior cavity 51; that is, where fluid is forced or delivered in the interior cavity 51 and then passes through the exit ports 56 formed in shell wall 63 to exit the tip electrode 17.

In some embodiments, the 3-D geometry includes one or more longitudinal passages 71 for a safety cord 72 passing therethrough as a safety measure against detachment of the tip electrode 17. The longitudinal passages 71 extend the length of the insert-molded portion 55 and have a U-bend 97 at or near the distal end of the insert-molded portion 55. In some embodiments, the safety cord 72 passes through the entire length of the catheter with a U-bend portion at the U-bend 97 and its proximal ends anchored within the control handle 16. In some embodiments, the proximal ends of the safety cord 72 are anchored at a more distal location, e.g., the bond joint at the distal end of the deflectable section 14.

In some embodiments, the 3-D geometry includes a distal face 81 configured with a recess 95 in which a thermistor 96 is insert-molded, and the insert-molded portion 55 configured with a longitudinal passage 73 through its length for the thermistor wires 41 and 42.

In some embodiments, the 3-D geometry includes the proximal portion 55P configured with a proximal extension 55E to the peripheral portion 57 of the interface portion 54 so that its outer surface 55S is flush with an outer surface 59 of the interface portion 54. Moreover, the outer surface 55S may be configured with a circumferential indentation 55C for accommodating ring electrode 21 which may be insert-molded. In some embodiments, the proximal portion 55P is configured with a notch 67 to allow passage of lead wire 30R from the ring electrode 21 into the lumen 29 of the connector tubing 23.

In some embodiments, the 3-D geometry includes a proximal face 79 of the insert-molded portion 55 configured with a recess 68 to receive a distal end of the resilient coupling member 91 of the force sensor 90. In the illustrated embodiment of FIG. 6A, the recess 68 is defined by a thin annular flange 69 that surrounds the distal end of the coupling member 91 in positioning the force sensor 90 on-axis with the longitudinal axis 84.

Figure 7B:
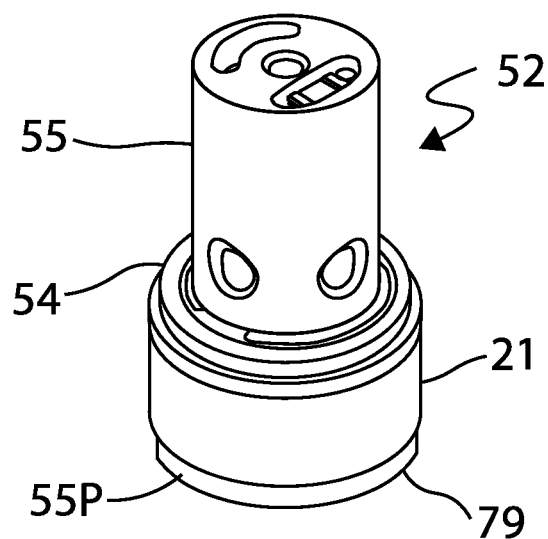
FIG. 7B is a perspective view of an insert member, in accordance with another embodiment of the present invention.

In some embodiments, the connector sleeve 23 housing the force sensor 90 is overmolded on the support member 52. In some embodiments, the connector sleeve 23 is overmolded on the proximal face 79 of the injection-molded portion 55, as shown in FIGS. 6A and 7B, to include an inner annular notch formation defined by an inner diameter at its distal end. In some embodiments, e.g., where the interface portion 54 is slid over the distal end of the connector sleeve 23, the connector sleeve 23 has an outer annular notch formation defined by an outer diameter suitable for sliding the interface portion 54 over it.

From the tip electrode 17, the lead wires 30T and 30R, and the thermistor wires 41 and 42 and the irrigation tubing 31 pass proximally through the lumen 92 of the coupling member 91, as shown in FIG. 6A, and into respective lumens of the tubing 19 of the intermediate section 14, as shown in FIG. 3. One or more of these components may be surrounded by one or more protective and/or insulating sleeves, as needed or desired. The lead wires, thermistor wires, and the irrigation tubing pass from the lumens of the tubing 19 of the intermediate section 14 and into the lumen 18 of the catheter body 12, as shown in FIG. 2.

Figure 7C:
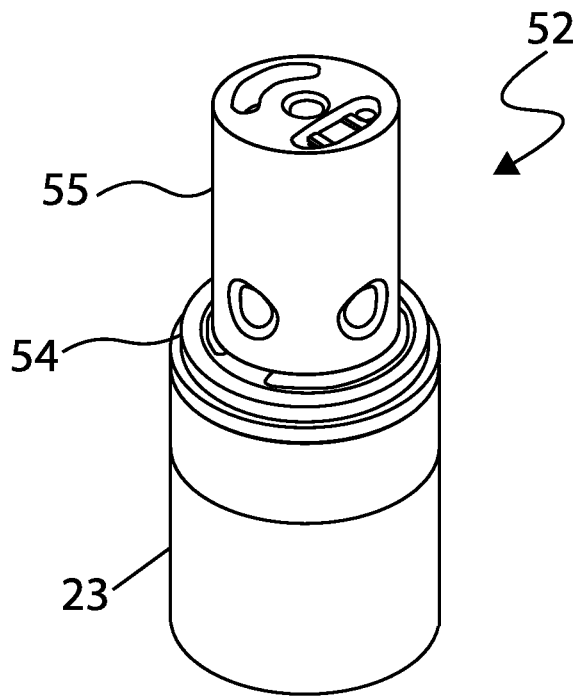
FIG. 7C is a perspective view of an insert member, in accordance with yet another embodiment of the present invention.

In some embodiments, with reference to and incorporation of the description above, the tip electrode is manufactured by processes that include:

(1) Providing the shell 50 of a suitable biocompatible metal alloy, the shell having a proximal rim 50P;

(2) Providing the support member 52 having an interface portion 54 and an insert-molded portion 55, including:
  (a) Providing a thin sheet of the same or similar suitable biocompatible metal alloy;
  (b) Configuring, for example, stamping, the thin sheet to form the interface portion 54; including one or more of the following:
    (i) forming an opening 61 with one or more interlock projections 62 and/or one or more electrical connection tab 54;
    (ii) forming a peripheral portion 57 with a step S having a distal (narrower) portion 57D and a proximal (wider) portion 57P, the distal portion 57D configured to provide an interference fit with the proximal rim 50P of the shell 50; and/or
    (iii) shaping the electrical connection tab 54, for example, bending the tab 54 at an angle such that the tab extends proximally;
  (c) Insert molding the insert-molded portion 55 onto the interface portion 54, including one or more of the following:
    (i) Micro-insert molding the member 55 with one or more of the following 3-D geometries:
      1. One or more fluid passages 65, including an axial passage 65A and/or a radial passage 65R;
      2. One or more fluid apertures 64, including a fluid aperture in fluid communication with a fluid passage;
      3. One or more longitudinal passages 71 and 73, including a longitudinal passage extending the length of the injection-molded member 55;
      4. Proximal extension 55E, including a proximal extension 55E having an outer surface even with an outer surface of the peripheral portion 57 of the interface portion 54;
      5. One or more circumferential indentations 55C, (see FIG. 7B) including a circumferential indentation 55C in the proximal extension 55E configured to receive a ring electrode 21, including an insert-molded ring electrode 21;
      6. Annular flange 69, including an annular flange on a proximal face, and an annular flange configured to receive a distal end of a force sensor coupling member 91;
      7. One or more notches 67, including a notch in the proximal extension 55E configured to pass a lead wire 30R for the ring electrode 21; and/or
      8. A recess 95, including a recess on a distal face of the insert-molded portion 55, including a recess configured to receive a thermistor 96.
    (ii) Micro-insert molding the ring electrode 21 in a circumferential indentation 55C (see FIG. 7B);
    (iii) Micro-insert molding the thermistor 96 in the recess 95.
    (iv) Over-molding the member 55 with a connector sleeve 23 (see FIG. 7C).

(3) Attaching the shell 50 to the interface portion 54, including:
  (a) Mounting the proximal rim 50P onto the distal portion 57D of the interface portion 54; and
  (b) Laser-welding the proximal rim 50P onto the peripheral portion 57.

It is understood that the terms "injection-molding," "insert-molding," and "over-molding," (and variations thereof) are used interchangeably herein, as appropriate, to include any process wherein a material is injected into a mold cavity, where it cools and hardens to the configuration of the cavity in forming a molded component. In some applications, the mold cavity is configured to partially or fully cover a first material or substrate in forming the molded component. In some applications, the mold cavity is configured in or through a first material or substrate in forming the molded component. Combinations of these applications may be employed as appropriate or desired.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Notably, the drawings are not necessarily to scale, and any one or more features of any one or more embodiments may be included in any other one or more embodiments in addition to or in lieu of any feature, as desired or appropriate. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrophysiology catheter having:
an elongated catheter body;
a control handle proximal of the catheter body;

a lead wire passing through the elongated catheter body; and a tip electrode distal of the catheter body, the tip electrode configured for irrigation and having a shell and a support member, the shell having a proximal opening and an interior cavity, the support member having an electrically-conductive interface portion of one material and an insert-molded portion of another material, the interface portion comprising a central opening in which the insert-molded portion is at least partially situated, the interface portion being in electrical connection with the shell via a peripheral portion engaged with the shell at the proximal opening, the interface portion comprising a connection tab extending proximally through the central opening of the interface portion and extending at least partially through the insert-molded portion, and the lead wire being connected to the connection tab.

2. The catheter of claim 1, wherein the insert-molded portion includes a distal portion in the interior cavity.

3. The catheter of claim 1, wherein the insert-molded portion includes a proximal portion proximal of the peripheral portion of the interface portion.

4. The catheter of claim 1, wherein the insert-molded portion has a fluid passage.

5. The catheter of claim 1, wherein the insert-molded portion has a fluid aperture.

6. The catheter of claim 1, wherein the insert-molded portion has a longitudinal passage.

7. The catheter of claim 1, wherein the insert-molded portion has a proximal extension.

8. The catheter of claim 1, wherein the insert-molded portion has a circumferential indentation.

9. The catheter of claim 1, wherein the insert-molded portion has an annular flange.

10. The catheter of claim 1, wherein the insert-molded portion has a notch.

11. The catheter of claim 1, wherein the insert-molded portion has a recess.

* * * * *